(12) United States Patent
Bindsell et al.

(10) Patent No.: US 7,537,617 B2
(45) Date of Patent: May 26, 2009

(54) BONE STRIP IMPLANTS AND METHOD OF MAKING SAME

(75) Inventors: James J. Bindsell, Germantown, TN (US); T. Andrew Simonton, Memphis, TN (US); Cary R. Reeves, Aledo, TX (US); William F. McKay, Memphis, TN (US); Eddie F. Ray, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 20 days.

(21) Appl. No.: 10/455,770

(22) Filed: Jun. 5, 2003

(65) Prior Publication Data

US 2004/0249463 A1    Dec. 9, 2004

(51) Int. Cl.
*A61F 2/44* (2006.01)
(52) U.S. Cl. .............. 623/17.16; 623/17.11; 623/23.51; 623/23.63
(58) Field of Classification Search ........................ None
See application file for complete search history.

(56) References Cited

U.S. PATENT DOCUMENTS

| | | | |
|---|---|---|---|
| 4,839,215 A | 6/1989 | Starling et al. ............... 428/131 |
| 4,950,296 A | 8/1990 | McIntyre ....................... 623/16 |
| 5,067,962 A | 11/1991 | Campbell et al. |
| 5,507,813 A | 4/1996 | Dowd et al. .................... 623/16 |
| 5,549,679 A | 8/1996 | Kuslich ........................ 623/17 |
| 5,571,189 A | 11/1996 | Kuslich ........................ 623/17 |
| 5,571,190 A | 11/1996 | Ulrich .......................... 623/17 |
| 5,676,146 A | 10/1997 | Scarborough ................ 128/654 |
| 5,895,426 A | 4/1999 | Scarborough et al. ......... 623/17 |
| 5,899,939 A | 5/1999 | Boyce et al. ................... 623/16 |
| 6,025,538 A | 2/2000 | Yaccarino ..................... 623/16 |
| 6,090,998 A | 7/2000 | Grooms et al. ................ 623/16 |
| 6,123,731 A | 9/2000 | Boyce et al. ............. 623/23.63 |
| 6,146,420 A | 11/2000 | McKay ........................ 623/17 |
| 6,200,347 B1 | 3/2001 | Anderson et al. ......... 623/16.11 |
| 6,270,528 B1 | 8/2001 | McKay ..................... 623/17.11 |
| 6,294,041 B1 | 9/2001 | Boyce et al. ............. 156/275.5 |
| 6,315,795 B1 | 11/2001 | Scarborough et al. ...... 623/7.11 |
| 6,371,988 B1 | 4/2002 | Pafford et al. ............. 623/17.11 |
| 6,379,385 B1 | 4/2002 | Kalas et al. ............... 623/17.11 |
| 6,409,765 B1 | 6/2002 | Bianchi et al. ............ 623/17.11 |
| 6,458,158 B1 | 10/2002 | Anderson et al. ......... 623/16.11 |
| 6,468,311 B2 | 10/2002 | Boyd et al. ............... 623/17.16 |
| 6,503,277 B2 | 1/2003 | Bonutti .................... 623/11.11 |
| 6,537,320 B1 * | 3/2003 | Michelson ............... 623/17.11 |
| 6,652,593 B2 * | 11/2003 | Boyer et al. ............. 623/23.63 |
| 6,752,831 B2 * | 6/2004 | Sybert et al. ............. 623/13.17 |
| 6,863,694 B1 * | 3/2005 | Boyce et al. ............. 623/23.63 |
| 2001/0020186 A1 | 9/2001 | Boyce et al. ............. 623/17.16 |
| 2001/0031254 A1 | 10/2001 | Bianchi et al. ............. 424/93.7 |
| 2001/0032017 A1 | 10/2001 | Alfaro et al. ............. 623/17.11 |
| 2001/0039456 A1 | 11/2001 | Boyer et al. ............. 623/23.52 |
| 2001/0039457 A1 | 11/2001 | Boyer et al. ............. 623/23.52 |

(Continued)

FOREIGN PATENT DOCUMENTS

DE    19504955    8/1996

(Continued)

*Primary Examiner*—David H Willse
*Assistant Examiner*—Javier G Blanco

(57) ABSTRACT

The present invention provides an implant for use in fusing adjacent bony structures. The implant comprises a plurality of bone pieces formed into at least one load bearing layer.

57 Claims, 3 Drawing Sheets

U.S. PATENT DOCUMENTS

| | | | |
|---|---|---|---|
| 2001/0039458 A1 | 11/2001 | Boyer et al. | 623/23.63 |
| 2001/0041941 A1 | 11/2001 | Boyer et al. | 623/23.52 |
| 2001/0049560 A1 | 12/2001 | Paul et al. | 623/17.16 |
| 2001/0056302 A1 | 12/2001 | Boyer et al. | 623/17.15 |
| 2002/0029082 A1 | 3/2002 | Muhanna | 623/17.11 |
| 2002/0029084 A1 | 3/2002 | Paul et al. | 623/23.63 |
| 2002/0045944 A1 | 4/2002 | Muhanna et al. | 623/17.16 |
| 2002/0062153 A1 | 5/2002 | Paul et al. | 623/17.11 |
| 2002/0082693 A1 | 6/2002 | Ahlgren | 623/17.11 |
| 2002/0091447 A1 | 7/2002 | Shimp et al. | 623/17.16 |
| 2002/0165612 A1 | 11/2002 | Gerber et al. | 623/17.11 |
| 2003/0045934 A1 | 3/2003 | Bonutti | 623/11.11 |
| 2003/0050708 A1 | 3/2003 | Bonutti | 623/23.57 |

FOREIGN PATENT DOCUMENTS

| | | |
|---|---|---|
| EP | 0141004 | 5/1985 |
| WO | WO 99/29271 | 6/1999 |
| WO | WO 00/30568 | 6/2000 |
| WO | WO 01/49220 | 7/2001 |
| WO | WO 01/66048 | 9/2001 |
| WO | WO 01/70136 | 9/2001 |
| WO | WO 01/78798 | 10/2001 |
| WO | WO 02/24233 | 3/2002 |
| WO | WO 02/056800 A2 | 7/2002 |
| WO | WO 02/064180 | 8/2002 |
| WO | WO 02/065957 | 8/2002 |
| WO | WO 02/069818 | 9/2002 |
| WO | WO 02/098329 | 12/2002 |
| WO | WO 02/098332 | 12/2002 |

* cited by examiner

BONE STRIP IMPLANTS AND METHOD OF MAKING SAME

BACKGROUND

Implants for use in fusing adjacent bony structures facilitate fusion by maintaining the adjacent bony structures in a predetermined spaced relationship while bone grows between them. In some cases these implants are formed from body tissues. In forming an implant from body tissue, a source of tissue, such as a bone, is formed into pieces meeting the desired shape and strength requirements for a particular implant. In the case of bone, the requirements are often specified in terms of a minimum wall thickness, minimum load bearing capacity, and/or geometric size and shape. A portion of the source tissue, including pieces removed in forming implants, will fall short of the requirements to form an integral implant. Thus, it is often difficult to obtain a high yield from a particular source.

SUMMARY

The present invention provides an implant for use in fusing adjacent bony structures.

In one aspect of the invention, an implant for use in fusing adjacent bony structures comprises a plurality of elongate bone pieces formed into at least one load bearing layer.

In another aspect of the invention, an implant for use in fusing adjacent bony structures comprises a plurality layers, each layer comprising a plurality of elongate bone pieces.

In another aspect of the invention, a method for use in fusing adjacent bony structures comprises the steps of combining a plurality of layers to form a layered implant, each layer comprising a plurality of elongate bone pieces and positioning the implant between adjacent bony structures in load bearing relationship.

In another aspect of the invention, an implant for use in fusing adjacent bony structures comprises a plurality of elongate bone pieces formed into at least one load bearing layer, at least some of the elongate bone pieces further comprising holes formed therethrough; and a flexible, elongate, biocompatible connecter, the connector being threaded through the holes to interconnect the pieces.

In another aspect of the invention, an implant for use in fusing adjacent bony structures comprises a plurality of elongate bone pieces formed into at least one load bearing layer, the elongate bone pieces being woven together.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DETAILED DESCRIPTION

Figure 1:
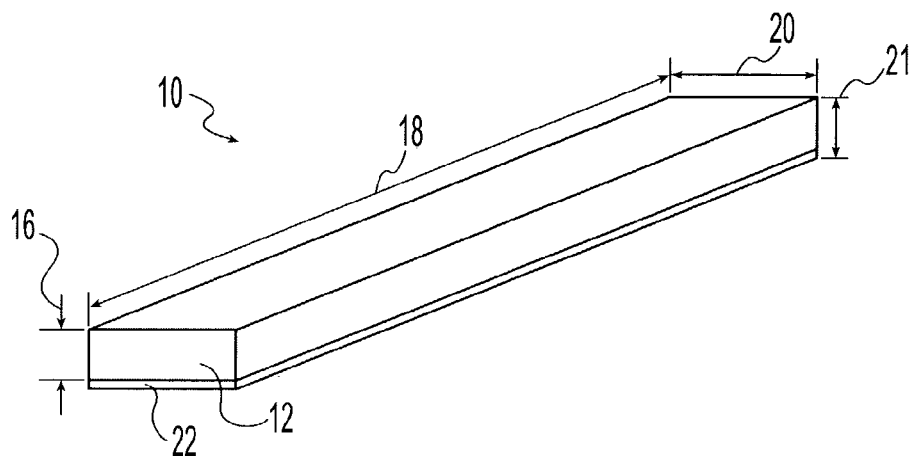
FIG. 1 is a perspective view of an illustrative embodiment of a bone piece used to make an implant according to the present invention.

Embodiments of a bone implant include a plurality of bone pieces formed into a load bearing implant for use in fusing adjacent bony structures. The adjacent bony structures may include vertebrae, long bones, and cranial bones, among others. Bone for the implant may be obtained from any suitable bone source including the implant recipient as in an autograft, another source of the same species as in an allograft, or a source of a different species as in a xenograft. Suitable examples of musculoskeletal tissue include humerus, tibia, femur, fibula, patella, ulna, radius, rib, vertebral bodies, etc. The bone pieces may be formed by machining, planing, grinding, grating, cutting, milling, splintering, chopping, crushing, and/or other suitable means for removing bone or reducing the source bone into smaller pieces. The pieces may be in the form of particles, random shaped chunks, fibers, strips and/or sticks of bone. Each of the bone pieces may comprise an elongated cortical bone layer running along substantially the entire length of the piece. The cortical bone layer may include a demineralized portion to give flexibility to the piece. Further, each cortical bone piece may have a predetermined cortical layer thickness or geometry less than a predetermined minimum wall thickness or geometry associated with an integral or assembled implant formed of the donor bone. Combining a plurality of bone pieces into an implant thereby allows donor bone having less than a predetermined minimum load bearing strength or geometry to be used to form a load-bearing implant.

The bone pieces may have any suitable longitudinal length, any suitable width, and any suitable height. Additionally, each of the plurality of pieces may further include a cancellous bone layer adjacent to the cortical bone layer along a portion or substantially all of the length of the piece. The plurality of pieces may be formed into a bone implant layer, mass or geometry, and one or more of the implant layers, masses or geometries may be formed into the load-bearing bone implant. The bone pieces in each bone implant layer, mass or geometry may be interconnected by weaving, pinning, suturing, pressing, incorporating a binding agent, collagen cross-linking, or any other method of interconnecting the pieces.

If the pieces are woven, the pieces may be woven together in a predetermined pattern to form a woven bone layer. The pieces may be partially or fully demineralized to facilitate weaving. The bone pieces oriented in one direction of the weave pattern may be demineralized more than the bone pieces in a second direction of the weave pattern so that the more demineralized pieces bend around the less demineralized pieces as they are woven. The pieces may further be segmentally demineralized at one or more spaced apart discrete portions such that each individual piece has a plurality of mineralized segments separated by relatively more flexible demineralized segments. The demineralized segments act like flexible hinges to facilitate the bending of the segmentally demineralized pieces around adjacent pieces in the weave pattern.

If the pieces are pinned, holes may be formed in the pieces and rigid pins made of bone, ceramic, metal, polymers, and/or other suitable materials may be pressed into the holes to interconnect the pieces.

If the pieces are sutured together, holes may be formed in the pieces and a flexible, elongate, biocompatible connector may be threaded through the holes to interconnect the pieces. The connector may be a suture and/or elongate pieces of body tissue. Examples of materials for such connectors include pericardium, demineralized bone, fascia, cartilage, tendon, ligament, skin, collagen, elastin, reticulum, intestinal submucosa, metal, resorbable polymer, and nonresorbable polymer, and/or other suitable material.

If a binding agent is used to interconnect the pieces, it may be an adhesive binding agent, a cementitious binding agent, and/or other suitable binding agent. Examples of adhesive binding agents include fibrin glue, cyanoacrylate, epoxy, polymethylmethacrylate, gelatin based adhesives, and other suitable adhesives and combinations thereof. Examples of cementitious binding agents include settable ceramics, calcium carbonate, calcium phosphate, plaster, and other suitable materials and combinations thereof.

If the pieces are interconnected by collagen cross-linking, the bone pieces may be partially demineralized to expose collagen fibers which may then be crosslinked by application of heat, pressure, chemicals, and/or other suitable cross-linking means.

Additionally, if a plurality of implant layers is utilized, they may be formed such as by folding or rolling a single layer to form multiple layers or by stacking multiple single layers adjacent to one another. The plurality of layers may be secured together by one or more of the interconnection mechanisms already described. Implants having one or more layers may have a layer axis substantially normal to the one or more layers and a load bearing axis along which load is applied to the implant from the adjacent bony structures. The implant may be oriented with its layer axis substantially perpendicular to, substantially parallel to, or at some other suitable angle to the load bearing axis. A layer made of elongate bone pieces may be arranged so that the bone pieces are arranged with their longitudinal axes substantially parallel to one another. This uni-directional layer may then be oriented in the implant with the longitudinal axes of the bone pieces substantially perpendicular to, substantially parallel to, or at some other suitable angle to the load bearing axis. For example, the bone pieces could derive from a long bone source and be oriented in a layer with their longitudinal axes substantially parallel to the implant load bearing axis so that the individual pieces are loaded similarly to how they were naturally loaded in the source bone.

The implant may further include one or more openings through the implant to facilitate fusion of the adjacent bony structures. The one or more openings may be formed by drilling, cutting, punching, or other suitable means. The implant may further include one or more bone growth promoting materials within the one or more layers, between the layers, and/or in the one or more openings, if present. Examples of bone growth promoting materials include growth factors, osteogenic proteins, bone morphogenic proteins, including human recombinant bone morphogenic proteins, LIM mineralization proteins, bone paste, bone chips, demineralized bone, hydroxyapatite, hormones, platelet derived growth factors, bone marrow aspirate, stem cells, and/or other suitable bone growth promoting materials.

Referring to the drawing, FIG. 1 depicts an illustrative piece of bone 10 having an elongate strip or stick form. The piece 10 has an elongate cortical bone layer 12 running along substantially the entire length of the strip. The piece 10 has a cortical layer thickness 16, length 18, and width 20. The piece may have a predetermined cortical layer thickness 16 less than a predetermined minimum wall thickness or geometry associated with an integral or assembled implant formed of the donor bone. The piece may further include a cancellous bone layer 22 adjacent to the cortical bone layer 12 along a portion or substantially all of the length of the piece yielding an overall implant thickness 21 greater than the cortical thickness 16.

Figure 2:
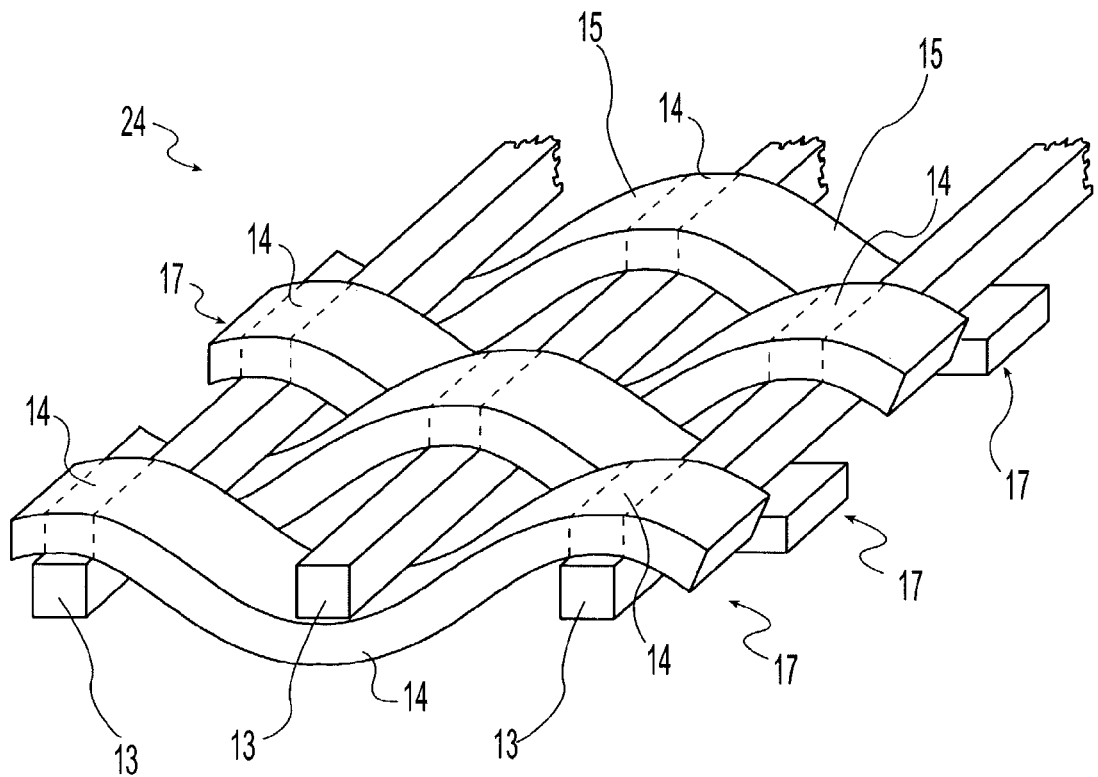
FIG. 2 is a perspective view of a load bearing layer for an implant made from a bone piece as in FIG. 1.

FIG. 2 depicts an illustrative implant layer 24 formed by weaving together individual elongate pieces of bone. The weave pattern includes warp pieces 13 oriented in a first direction and filler pieces 17 oriented in a second direction. Both the warp pieces 13 and the filler pieces 17 may comprise the elongate bone pieces of FIG. 1. The pieces 13,17 may be sufficiently flexible to permit weaving. Alternately, weaving may be facilitated by partially demineralizing the pieces. In the illustrated embodiment, only a portion 14 of the pieces has been demineralized to form segmentally demineralized bone pieces having one or more spaced apart discrete demineralized portions 14 such that each individual piece 10 has a plurality of mineralized segments 15 separated by relatively more flexible demineralized segments 14. The demineralized segments act like flexible hinges to facilitate the bending of the segmentally demineralized pieces around adjacent pieces in the weave pattern. Both the warp 13 and filler 17 pieces can be demineralized or one can be demineralized and the other left fully mineralized as illustrated.

Figure 3:
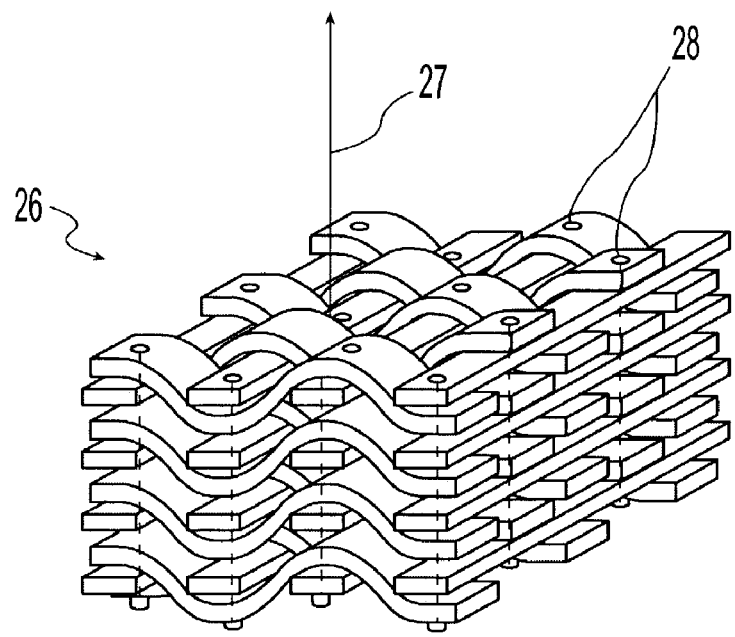
FIG. 3 is a perspective view of a multi-layered implant made by repeatedly stacking load bearing layers as in FIG. 2 to form a thicker implant.

One or more implant layers, whether woven or otherwise formed, may be formed into a bone implant. FIG. 3 depicts an illustrative implant 26 comprising a plurality of individually woven layers, described relative to FIG. 2, stacked together to form a thicker implant. The layers are interconnected by an interconnection mechanism 28 comprising rigid bone pins pressed into holes formed in the layers. The implant has a layer axis 27 normal to the layers.

Figure 4:
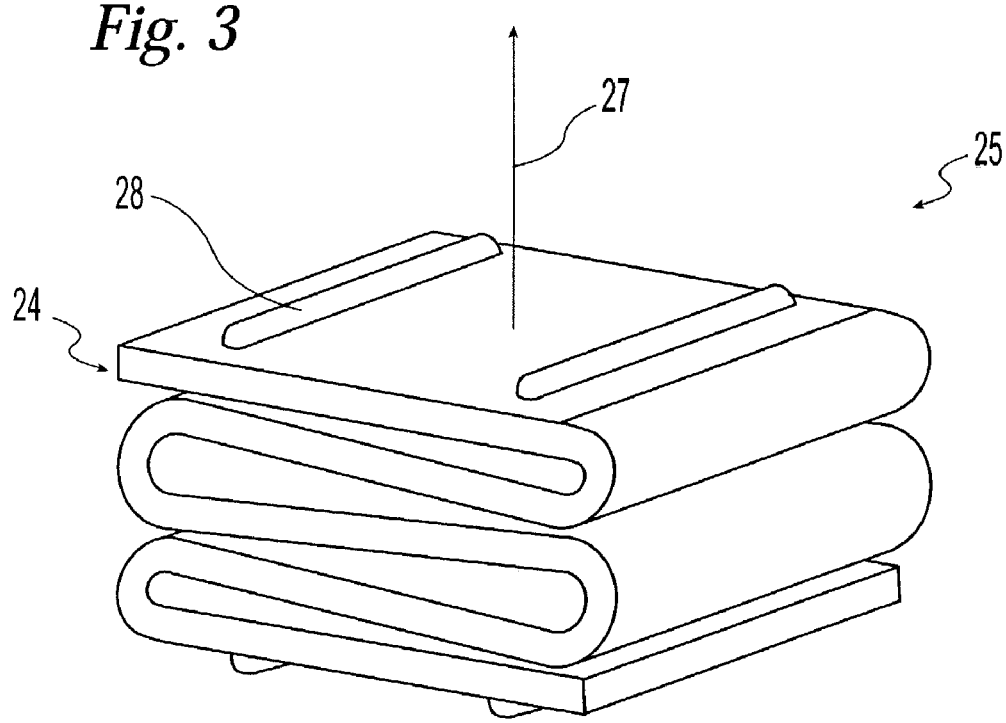
FIG. 4 is a perspective view of a multi-layered implant made by folding back on itself a load bearing layer as in FIG. 2 to form a thicker implant.

FIG. 4 depicts an illustrative implant 25 comprising a single layer 24 folded back on itself to form a plurality of layers. The layer 24 comprises a plurality of bone pieces of any suitable shape interconnected in any suitable manner. The layers in this illustrative embodiment are interconnected by an interconnection mechanism 28 comprising an elongate flexible connector threaded through holes formed in the layers. The implant has a layer axis 27 normal to the layers.

Figure 5:
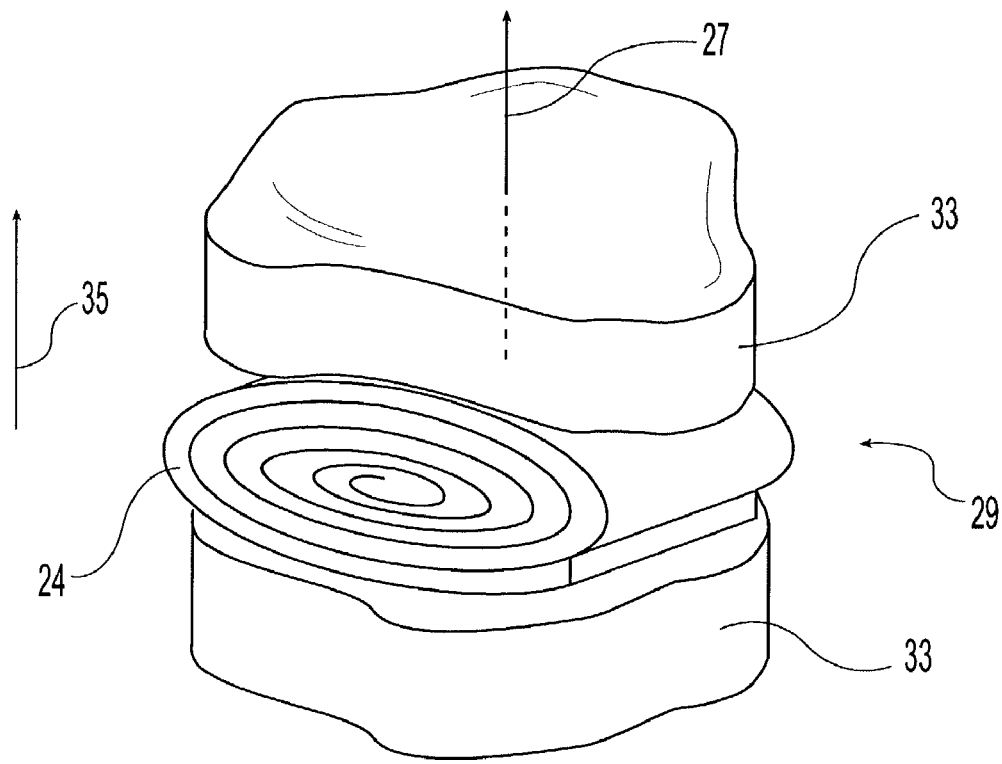
FIG. 5 is a perspective view of a multi-layered implant made by rolling up a load bearing layer as in FIG. 2 to form a thicker implant.
Figure 6:
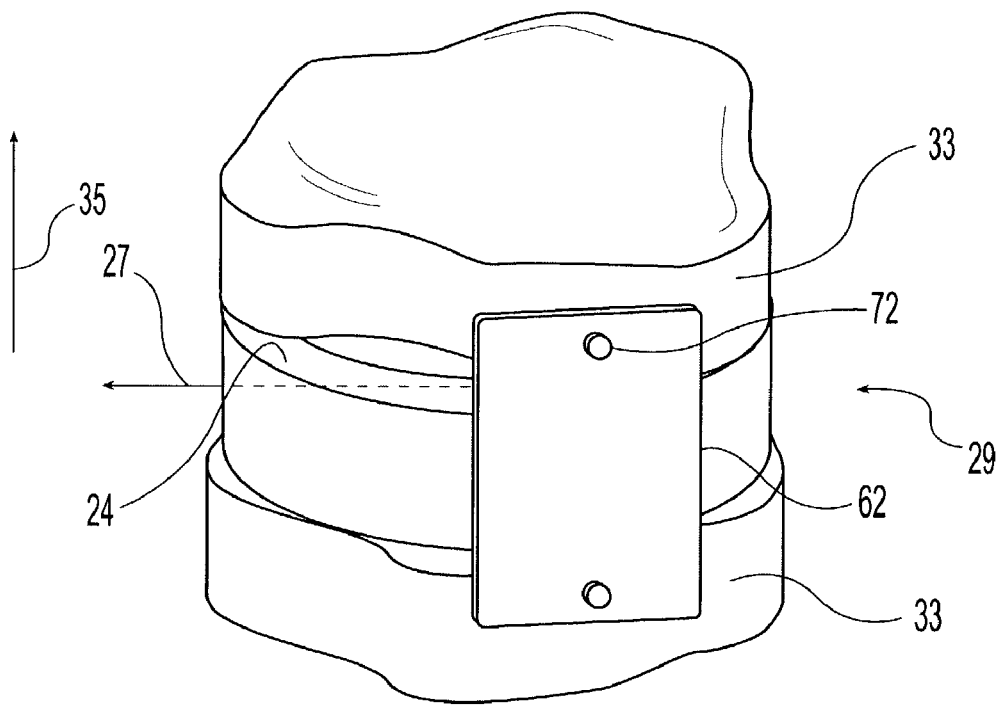
FIG. 6 is a perspective view of a multi-layered implant like that of FIG. 5 but oriented perpendicularly to that of FIG. 5 and also depicting its use in conjunction with supplemental fixation device mounted on a bone.

FIGS. 5 and 6 depict an illustrative implant 29 comprising a single layer 24 rolled to form a plurality of layers overlying one another radially in a substantially cylindrical wound spiral construct. The implant 29 has a layer axis 27 normal to the layers. FIG. 5 depicts the implant 29 in load bearing relationship to adjacent bony structures 33 with the layer axis 27 substantially parallel to the load bearing axis 35. FIG. 6 depicts the implant 29 in load bearing relationship to adjacent bony structures 33 with the layer axis 27 substantially perpendicular to the load bearing axis 33. A supplemental fixation device 62 may be used in conjunction the implant 29. The fixation device 62 may include one or more anchor mechanisms 72, such as screws, pins, wires, and/or other mechanisms for attaching it to the adjacent bony structures 33 to limit the relative motion between them. The fixation device 62 may substantially prevent all relative motion, or it may allow a predetermined amount of motion, such as to allow the implant 29 to remain in contact with the adjacent bony structures 33 during the healing and fusion processes. Suitable examples of a fixation device 62 include plates, internal or external rod systems, cable systems, cerclage systems, screws, and other suitable devices and combinations thereof.

The plurality of bone pieces comprising cortical bone may have a predetermined layer thickness and geometry, measured radially from the longitudinal axis of the donor bone, less than a predetermined minimum wall thickness and geometry. For example, the predetermined layer thickness and geometry may be in the range of less than 2 mm thick in one embodiment, less than 1.8 mm thick in another embodiment, less than 1.5 mm thick in yet another embodiment, less than 1.0 mm thick in still another embodiment, and less than 0.5 mm thick in another embodiment. Further, for example, the predetermined minimum wall thickness and geometry may relate to a minimum acceptable thickness or geometry associated with forming an integral or assembled load bearing implant. The predetermined minimum cortical geometry may vary depending on the application. For example, a minimum geometry for use in the cervical spine may be substantially less than a minimum cortical geometry for the lumbar spine. For instance, a predetermined minimum wall thickness or geometry for integral or assembled cortical wedge cervical spine implant, such as may be formed from a fibula, may be 3.0 mm in one embodiment, 2.5 mm in another embodiment, 2.0 mm in yet another embodiment, and 1.8 mm in still another embodiment. On the other hand, a minimum cortical geometry for an integral or assembled lumbar implant may be 4.5 mm in one embodiment, 4.0 mm in another embodiment, and 3.5 mm in another embodiment.

Implants formed from a plurality of bone pieces may have a compressive strength, or load bearing capability, in the range of 50N to 20,000N. For instance, embodiments may have compressive strength greater than 70N, or greater than 800N, or greater than 1000N, or greater than 1200N, or greater than 3000N, or greater than 5000N, or greater than 7000N, or greater than 10,000N, or greater than 12,000N, or greater than 15,000N, or greater than 17,000N. This compressive strength provides load-bearing capability greater than typical cancellous bone and up to that of typical cortical bone.

Bone may be obtained from any suitable bone source including the implant recipient as in an autograft, another source of the same species as in an allograft, or a source of a different species as in a xenograft. Suitable examples of musculoskeletal tissue include humerus, tibia, femur, fibula, patella, ulna, radius, rib, vertebral bodies, etc. The bone pieces may be machined, milled, cut, planed, grated, crushed, splintered and/or otherwise removed and/or formed from the donor bone.

Although embodiments of implants and methods of making implants have been described and illustrated in detail, it is to be understood that the same is intended by way of illustration and example only and is not to be taken by way of limitation. Accordingly, variations in and modifications to the implants and methods will be apparent to those of ordinary skill in the art, and the following claims are intended to cover all such modifications and equivalents.

What is claimed is:

1. A load bearing spinal implant for use in fusing adjacent vertebrae, the implant effective to bear loads occurring between the adjacent vertebrae and comprising a plurality of elongate sticks of bone cut from a source bone to have a longitudinal length, a height, and a width, wherein said elongate sticks of bone are woven together to form at least one load bearing layer, wherein said load bearing layer includes a first group of said sticks of bone oriented in a first direction and a second group of said sticks of bone oriented in a second direction angled relative to the first direction, the second group of sticks comprising fully mineralized bone having no demineralized bone segments; and wherein said spinal implant has a compressive strength greater than 70 Newtons and is sized to span between and contact the adjacent vertebrae; and wherein the sticks of said first group are segmentally demineralized to include a plurality of mineralized segments separated by relatively more flexible demineralized segments, wherein said demineralized segments overlie portions of the sticks of said second group and functions as flexible hinges that facilitate bending of the sticks of said first group around the sticks of said second group, and wherein the individual elongate sticks of bone comprise an elongate cortical bone layer and a cancellous bone layer adjacent to the cortical bone layer, each layer running along substantially the entire length of the stick.

2. The implant of claim 1 wherein the elongate sticks of bone are interconnected by at least one interconnection mechanism selected from the group consisting of pinning, suturing, pressing, incorporating a binding agent, and crosslinking exposed collagen fibers.

3. The implant of claim 1 wherein the elongate sticks of bone are interconnected by a biocompatible adhesive.

4. The implant of claim 3 wherein the adhesive comprises at least one adhesive selected from the group consisting of fibrin glue, cyanoacrylate, epoxy, polymethylmethacrylate, and gelatin based adhesives.

5. The implant of claim 1 wherein the elongate sticks of bone are interconnected by at least one binding agent selected from the group consisting of settable ceramics, calcium carbonate, calcium phosphate, apatite, hydroxyapatite, and plaster.

6. The implant of claim 1 wherein the elongate sticks of bone further comprise exposed collagen and the exposed collagen of adjacent pieces is crosslinked to interconnect the elongate sticks of bone.

7. The implant of claim 1 wherein at least some of the elongate sticks of bone further comprise holes formed therethrough and a flexible, elongate, biocompatible connecter, the connector being threaded through the holes to interconnect the pieces.

8. The implant of claim 7 wherein the connector comprises at least one connector selected from the group consisting of elongate pieces of body tissue and sutures.

9. The implant of claim 7 wherein the connector comprises at least one material selected from the group consisting of pericardium, demineralized bone, fascia, cartilage, tendon, ligament, skin, collagen, elastin, reticulum, intestinal submucosa, metal, resorbable polymer, and nonresorbable polymer.

10. The implant of claim 1 wherein the individual sticks of bone have less than a predetermined minimum load bearing capacity and the combined pieces form an implant that achieves a predetermined load bearing capacity greater than the predetermined minimum load bearing capacity.

11. The implant of claim 1 wherein the individual sticks of bone have a predetermined geometry outside of a predetermined standard associated with a unitary implant and the combined pieces form an assembled implant that achieves the predetermined geometry.

12. The implant of claim 1 further comprising a predetermined cortical layer thickness less than a predetermined minimum thickness for an integral bone implant.

13. The implant of claim 1 further comprising a layer axis substantially normal to the layer and a load bearing axis along which load is applied to the implant from the adjacent vertebrae, the layer axis being substantially parallel to the load bearing axis.

14. The implant of claim 1 further comprising a layer axis substantially normal to the layer and a load bearing axis along which load is applied to the implant from the adjacent vertebrae, the layer axis being substantially perpendicular to the load bearing axis.

15. The implant of claim 1 wherein each of the sticks of bone has a longitudinal axis and the sticks in the first group are arranged in the layer with their longitudinal axes being substantially parallel.

16. The implant of claim 15 further comprising a load bearing axis along which load is applied to the implant from the adjacent vertebrae, the longitudinal axes of the plurality of sticks of bone being substantially perpendicular to the load bearing axis.

17. The implant of claim 15 further comprising a load bearing axis along which load is applied to the implant from the adjacent vertabrae, the longitudinal axes of the plurality of sticks of bone being substantially parallel to the load bearing axis.

18. The implant of claim 1 comprising a plurality of layers, each layer comprising a plurality of elongate sticks of bone.

19. The implant of claim 18 wherein the plurality of layers comprises a plurality of radial layers formed by rolling a single layer into a substantially cylindrical shape.

20. The implant of claim 19 wherein each layer comprises a plurality of elongate sticks of bone woven together, the implant being formed by first weaving the elongate sticks of bone to form a single layer and then rolling the single layer into a substantially cylindrical shape.

21. The implant of claim 18 wherein the plurality of layers comprises a single layer folded back on itself at least once to form the plurality of layers.

22. The implant of claim 21 wherein each layer comprises a plurality of elongate sticks of bone woven together, the implant being formed by first weaving the elongate sticks of bone to form a single layer and then folding the layer back on itself one or more times.

23. The implant of claim 18 wherein the plurality of layers comprises a stack of individual discrete layers.

24. The implant of claim 23 wherein each layer comprises a plurality of elongate sticks of bone woven together.

25. The implant of claim 18 further comprising one or more interconnection mechanisms securing the layers together.

26. The implant of claim 25 further comprising at least one interconnection mechanism selected from the group consisting of pinning, suturing, pressing, incorporating a binding agent, and cross-linking exposed collagen fibers.

27. The implant of claim 25 wherein the layers are interconnected by a biocompatible adhesive binding agent.

28. The implant of claim 27 wherein the adhesive comprises at least one adhesive selected from the group consisting of fibrin glue, cyanoacrylate, epoxy, polymethylmethacrylate, and gelatin based adhesives.

29. The implant of claim 25 wherein the layers are interconnected by at least one binding agent selected from the group consisting of settable ceramics, calcium carbonate, calcium phosphate, apatite, hydroxyapatite, and plaster.

30. The implant of claim 25 wherein the layers further comprise exposed collagen and the exposed collagen of adjacent layers is crosslinked to interconnect the layers.

31. The implant of claim 25 further comprising an elongate biocompatible connector, the connector being threaded through the layers to interconnect the layers.

32. The implant of claim 31 wherein the connector comprises at least one connector selected from the group consisting of elongate pieces of body tissue and sutures.

33. The implant of claim 31 wherein the connector comprises at least one material selected from the group consisting of pericardium, demineralized bone, fascia, cartilage, tendon, ligament, skin, collagen, elastin, reticulum, intestinal submucosa, metal, resorbable polymer, and nonresorbable polymer.

34. The implant of claim 25 further comprising one or more openings through the implant to facilitate the fusion of the adjacent bony structures.

35. The implant of claim 34 further comprising a bone growth promoting material within the one or more openings.

36. The implant of claim 35 wherein the bone growth promoting material comprises at least one material selected from the group comprising bone derived growth factors, osteogenic proteins, bone morphogenic proteins, human recombinant bone morphogenic proteins, LIM mineralization proteins, bone paste, bone chips, demineralized bone, hydroxyapatite, hormones, and platelet derived growth factor.

37. The implant of claim 18 wherein the plurality of layers overlie one another along a layer axis normal to the layers, the implant further comprising a load bearing axis along which load is applied to the implant from the adjacent bony structures, the layer axis being substantially parallel to the load bearing axis.

38. The implant of claim 37 wherein the layers overlie one another radially in a wound spiral construct.

39. The implant of claim 37 wherein the layers comprise a single layer folded back on itself one or more times.

40. The implant of claim 37 wherein the layers comprise a stack of individual discrete layers.

41. The implant of claim 18 wherein the plurality of layers overlie one another along a layer axis substantially normal to the layers, the implant further comprising a load bearing axis along which load is applied to the implant from the adjacent bony structures, the layer axis being substantially perpendicular to the load bearing axis.

42. The implant of claim 41 wherein the layers overlie one another radially in a wound spiral construct.

43. The implant of claim 41 wherein the layers comprise a single layer folded back on itself one or more times.

44. The implant of claim 41 wherein the layers comprise a stack of individual discrete layers.

45. The implant of claim 1 further comprising a fixation device attached to said adjacent bony structures to limit relative motion therebetween.

46. A load bearing spinal implant for use in fusing adjacent vertebrae, the implant effective to bear loads occurring between the adjacent vertebrae and comprising at least one layer, said layer comprising a plurality of sticks of bone cut from a source bone and having a substantially rectangular cross section, wherein said elongate sticks of bone are interconnected to one another by weaving to form at least one load bearing layer, and wherein the implant has a compression strength of at least 70 Newtons and is sized to span between and contact the adjacent vertebrae;

wherein said layer includes a first group of said sticks of bone oriented in a first direction and a second group of said sticks of bone oriented in a second direction angled relative to the first direction, the second group of sticks comprising fully mineralized bone having no demineralized bone segments;

wherein the sticks of said first group are segmentally demineralized to include a plurality of mineralized segments separated by relatively more flexible demineralized segments, and wherein said demineralized segments overlie portions of the sticks of said second group and function as flexible hinges that facilitate bending of the sticks of said first group around the sticks of said second group; and wherein the individual elongate sticks of bone comprise an elongate cortical bone layer and a cancellous bone layer adjacent to the cortical bone layer, each layer running along substantially the entire length of the stick.

47. The implant of claim 46 wherein the implant comprises a plurality of layers that overlie one another radially in a wound spiral construct.

48. The implant of claim 46 wherein the implant comprises a plurality of layers formed by a single layer folded back on itself one or more times.

49. The implant of claim 46 comprising a plurality of layers, wherein the layers comprise a stack of individual discrete layers.

50. The implant of claim 46 further comprising a fixation device attached to said adjacent bony structures to limit relative motion therebetween.

51. A load bearing spinal implant for use in fusing adjacent bony structures, the implant effective to bear loads occurring between the adjacent bony structures and comprising: a plurality of elongate sticks of bone formed into at least one load bearing layer by weaving, at least some of the elongate sticks of bone further comprising holes formed therethrough; and a flexible, elongate, biocompatible connector, the connector being threaded through the holes to interconnect the pieces:

wherein said layer includes a first group of said sticks of bone oriented in a first direction and a second group of said of bone oriented in a second direction angled relative to the first direction, the second group of sticks comprising fully mineralized bone having no demineralized bone segments;

wherein the sticks of said first group are segmentally demineralized to include plurality of mineralized segments separated by relatively more flexible demineralized segments, and wherein said demineralized segments overlie portions of the sticks of said second group and function as flexible hinges that facilitate bending of the sticks of said first group around the sticks of said second group; and wherein the individual elongate sticks of bone comprise an elongate cortical bone layer and a cancellous bone layer adjacent to the cortical bone layer, each layer running along substantially the entire length of the stick.

52. The implant of claim 51 wherein the connector comprises at least one connector selected from the group consisting of elongate pieces of body tissue and sutures.

53. The implant of claim 51 wherein the connector comprises at least one material selected from the group consisting of pericardium, demineralized bone, fascia, cartilage, tendon, ligament, skin, collagen, elastin, reticulum, intestinal submucosa, metal, resorbable polymer, and nonresorbable polymer.

54. The implant of claim 51 further comprising a fixation device attached to said adjacent bony structures to limit relative motion therebetween.

55. A load bearing spinal implant for use in fusing adjacent vertebrae, the implant effective to bear loads occurring between the adjacent vertebrae and comprising a plurality of elongate sticks of bone formed into at least one load bearing layer, the elongate sticks of bone being woven together to form at least one load bearing layer, the implant has a compressive strength greater than 70 Newtons and is sized to span between and contact the adjacent vertebrae;

wherein said layer includes a first group of said sticks of bone oriented in a first direction and a second group of said sticks of bone oriented in a second direction angled relative to the first direction, the second group of sticks comprising fully mineralized bone having no demineralized bone segments;

wherein the sticks of said first group are segmentally demineralized to include plurality of mineralized segments separated by relatively more flexible demineralized segments, and wherein said demineralized segments overlie portions of the sticks of said second group and function as flexible hinges that facilitate bending of the sticks of said first group around the sticks of said second group; and wherein the individual elongate sticks of bone comprise an elongate cortical bone layer and a cancellous bone layer adjacent to the cortical bone layer, each layer running along substantially the entire length of the stick.

56. The implant of claim 55 wherein at least some of the elongate sticks of bone of the second group comprise a cortical bone layer and a cancellous bone layer adjacent to the cortical bone layer, each layer running along substantially their entire length.

57. The implant of claim 55 further comprising a fixation device attached to said adjacent vertebrae to limit relative motion therebetween.

* * * * *